(12) United States Patent
Galiano

(10) Patent No.: US 11,326,198 B2
(45) Date of Patent: May 10, 2022

(54) METHOD TO IDENTIFY MICROORGANISMS USING SPECTROSCOPIC TECHNIQUE

(71) Applicant: ALIFAX S.R.L., Polverara (IT)

(72) Inventor: Paolo Galiano, Padua (IT)

(73) Assignee: ALIFAX S.R.L., Polverara (IT)

( * ) Notice: Subject to any disclaimer, the term of this patent is extended or adjusted under 35 U.S.C. 154(b) by 0 days.

(21) Appl. No.: 16/967,129

(22) PCT Filed: Jan. 31, 2019

(86) PCT No.: PCT/IT2019/050025
§ 371 (c)(1),
(2) Date: Aug. 3, 2020

(87) PCT Pub. No.: WO2019/150408
PCT Pub. Date: Aug. 8, 2019

(65) Prior Publication Data
US 2020/0354766 A1    Nov. 12, 2020

(30) Foreign Application Priority Data
Feb. 2, 2018   (IT) .................. 102018000002353

(51) Int. Cl.
*C12Q 1/04* (2006.01)
*G01N 21/35* (2014.01)
*G01N 21/552* (2014.01)

(52) U.S. Cl.
CPC ............... *C12Q 1/04* (2013.01); *G01N 21/35* (2013.01); *G01N 21/552* (2013.01); *G01N 2021/3595* (2013.01); *G01N 2201/1293* (2013.01)

(58) Field of Classification Search
CPC ........ C12Q 1/04; G01N 21/35; G01N 21/552; G01N 2021/3595; G01N 2201/1293
See application file for complete search history.

(56) References Cited

U.S. PATENT DOCUMENTS

| | | | |
|---|---|---|---|
| 6,379,920 B1 * | 4/2002 | El-Sayed | C12Q 1/02 435/29 |
| 2005/0143936 A1 * | 6/2005 | Laughlin | G01N 21/3563 702/23 |
| 2019/0178793 A1 * | 6/2019 | Ismail | G01N 21/552 |

\* cited by examiner

*Primary Examiner* — Hugh Maupin
(74) *Attorney, Agent, or Firm* — Marshall, Gerstein & Borun LLP

(57) ABSTRACT

A method to classify and identify microorganisms using the FTIR ATR technique.

14 Claims, 5 Drawing Sheets

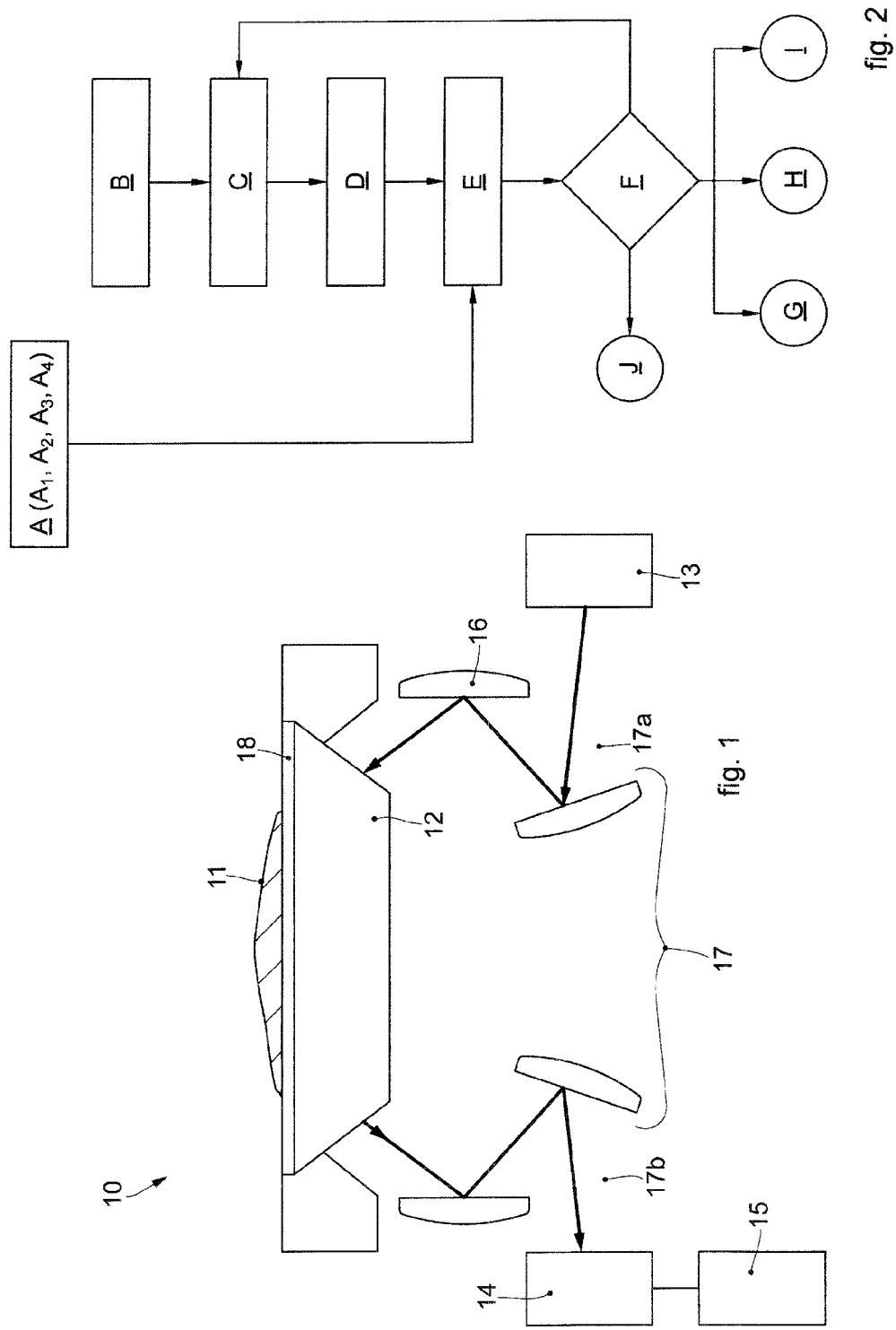

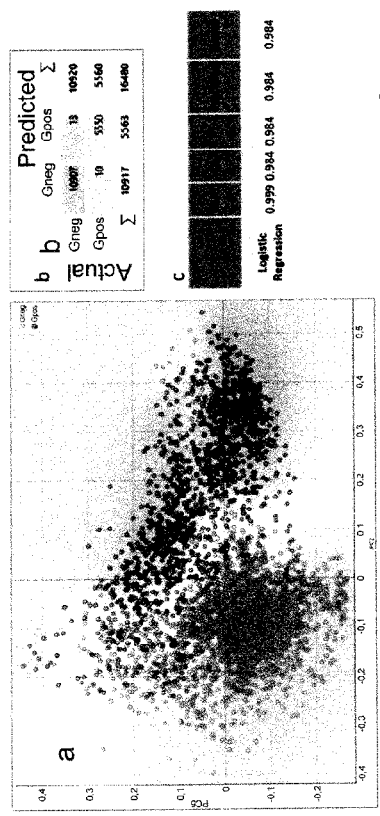

fig. 7

Confusion matrix obtained through logistical regression (showing the proportion of actual data)

| | PREDICTED | | | | | | | | | | | |
|---|---|---|---|---|---|---|---|---|---|---|---|---|
| ACTUAL | Acinetobacter | Enterococcus | Escherichia | Klebsiella | Proteus | Staphylococcus | Citrobacter | Enterobacter | Morganella | Pseudomonas | Serratia | Stenotrophomonas | Streptococcus | Σ |
| Acinetobacter | | 0,0% | 0,0% | 0,0% | 0,0% | 0,4% | 0,0% | 0,0% | 0,0% | 0,0% | 0,0% | 0,0% | 0,0% | 2310 |
| Enterococcus | 0,0% | | 0,1% | 0,0% | 0,0% | 0,0% | 0,0% | 0,0% | 0,0% | 0,0% | 0,0% | 0,0% | 0,0% | 3390 |
| Escherichia | 0,0% | 0,0% | | 0,4% | 0,2% | 0,0% | 0,2% | 0,0% | 0,0% | 0,0% | 0,2% | 0,0% | 0,0% | 2250 |
| Klebsiella | 0,0% | 0,0% | 0,9% | | 0,0% | 0,0% | 0,0% | 0,5% | 0,5% | 0,0% | 0,4% | 0,0% | 0,0% | 3700 |
| Proteus | 0,0% | 0,0% | 0,1% | 0,0% | | 0,0% | 0,1% | 0,2% | 1,1% | 0,0% | 0,0% | 0,0% | 0,0% | 1230 |
| Staphylococcus | 0,0% | 0,0% | 0,0% | 0,0% | 0,0% | | 0,0% | 0,0% | 0,0% | 0,0% | 0,0% | 0,0% | 0,0% | 8450 |
| Citrobacter | 0,0% | 0,3% | 0,2% | 0,1% | 0,4% | 0,0% | | 0,3% | 0,0% | 0,0% | 0,1% | 0,0% | 0,0% | 1230 |
| Enterobacter | 0,0% | 0,0% | 0,6% | 0,0% | 0,8% | 0,0% | 0,3% | | 0,0% | 0,0% | 0,0% | 0,0% | 1,8% | 2460 |
| Morganella | 0,0% | 0,0% | 0,0% | 0,1% | 0,0% | 0,0% | 0,2% | 0,0% | | 0,0% | 0,0% | 0,0% | 0,0% | 1230 |
| Pseudomonas | 0,0% | 0,0% | 0,5% | 1,9% | 0,7% | 0,0% | 0,0% | 0,2% | 0,0% | | 0,0% | 0,1% | 0,0% | 2670 |
| Serratia | 0,0% | 0,0% | 0,0% | 0,0% | 0,0% | 0,8% | 0,0% | 0,0% | 0,0% | 0,0% | | 0,0% | 0,0% | 1230 |
| Stenotrophomonas | 0,0% | 0,0% | 0,0% | 0,0% | 0,0% | 0,2% | 0,0% | 0,0% | 0,0% | 0,0% | 0,1% | | 0,2% | 1230 |
| Streptococcus | 0,0% | 0,0% | 0,0% | 0,0% | 0,0% | 0,0% | 0,0% | 0,0% | 0,0% | 0,0% | 0,0% | 0,0% | | 1740 |
| Σ | 2301 | 3391 | 2284 | 3671 | 1235 | 8472 | 1234 | 2420 | 1242 | 2663 | 1203 | 1222 | 1782 | 33120 | fig. 8

METHOD TO IDENTIFY MICROORGANISMS USING SPECTROSCOPIC TECHNIQUE

FIELD OF THE INVENTION

The present invention concerns a method to identify microorganisms using statistical techniques, such as for example the technique of multivariate analysis of spectral profiles, or alternatively neural networks, to obtain indications relating to the growth of microorganisms in extremely short times compared to conventional methods.

In particular, the invention is based on the development of an analytical instrument to identify microorganisms through the analysis of the spectral profile ATR-FTIR of an unknown sample, and the comparison of the spectral profile with those of samples previously collected and memorized in a database.

BACKGROUND OF THE INVENTION

Fourier transform infrared spectroscopy (FTIR) is a non-destructive analysis technique, which allows to obtain information on the chemical composition of a sample analyzed. Since the beginning of the 1990s this technique has been used for the analysis of biological samples (Diem M. et al., The Analyst [27 Aug. 2004, 129 (10): 880-885]).

At the same time, the ability of the FTIR technique to identify and classify unknown microorganisms was shown (Helm D. et al., Journal of General Microbiology (1991, 137, 69-79) and Marley L. et al., Vibrational Spectroscopy 26, 2, 2001, 151-159).

The different species, subspecies or sub-classifications of microorganisms are characterized by a precise biochemical composition, in terms of proteins, lipids, nucleic acids and polysaccharides, which is reflected in a distinct vibrational spectrum (ed. Griffiths and Chalmers, 2001 Handbook of vibrational spectroscopy, John Wiley & sons, New York, Volume 5).

Some potential applications suggested by the FTIR technique in microbiology include:
(i) identification of pathogens in the human or veterinary field, for example in a clinical laboratory;
(ii) epidemiological investigations, topic of study, screening of pathogens, hygiene checks, elucidation of infectious chains, control therapies and detection of recurrent infections;
(iii) characterization and screening of microorganisms from the environment;
(iv) monitoring of biotechnological processes;
(v) microbiological quality control in food or pharmaceutical industries;
(vi) maintenance of harvested strains.

Methods to identify microorganisms are known, based on techniques of comparative analysis between the spectrum of an unknown sample and the spectra of known species of microorganisms, stored in a database.

Examples of known identification methods of this type are reported in documents U.S. Pat. No. 5,660,998A, CN103217398A, U.S. Pat. No. 6,379,920B1, WO2006002537A1, U.S. Pat. No. 9,551,654B2, US20170167973A1, WO2017/210783A1, Sousa et al., European Journal of Clinical Microbiology & Infectious Diseases (2014) 33: 1345-1353, Whittaker et al., Journal of Microbiological Methods 55 (2003) 709-716, Wang et al., International Journal of Food Microbiology 167 (2013) 293-302.

In many of the known methods, however, spectra acquisition is performed in transmission, reflection, or imaging modes.

For example, transmission or reflection acquisition modes are reported in U.S. Pat. Nos. 5,660,998 and 6,379,920, while imaging modes are adopted in WO2006002537A1, U.S. Pat. No. 9,551,654B2, US20170167973A1.

These methods have disadvantages connected to the fact that the signal obtained directly depends on the thickness and morphology of the sample, which may be too thick and generate saturation, or non-homogeneous and generate distortions due to scattering.

It is also known that methods based on imaging approaches, for example multipixel, may have limitations on the resolution of individual spectra, due to the lower signal to noise ratio obtainable per pixel, compared to single-point detectors.

Another disadvantage of the state of the art is that often the spectra can present signals due to the presence of water or other contaminants, which cover the peculiar signals of microorganisms.

In some cases, such as for example CN103217398A, drying procedures are adopted but, as reported in WO 2017/210783A1, these procedures can have significant and irreversible effects on the microorganisms, also modifying their spectra.

In some cases, such as for example WO 2017/210783 A1, it is possible to resort to multiple acquisitions to remove the water components present in the spectra. However, this solution has disadvantages connected to greater analysis time and greater complexity of the analytical procedures for comparing spectra.

Another disadvantage of the state of the art is that often the reference database comprises a limited number of species of microorganisms, and therefore does not cover a wide range of possible species.

By way of example, the database and the related identification method reported in CN103217398A refer to 13 bacterial species.

Moreover, with the increase in sizes of the reference databases, a series of problems relating to the procedures for cultivating and growing the species of microorganisms comes into being, to the procedures for acquiring the spectra and to the comparative analysis procedures.

For example, as the size of the database increases, the analysis time of the unknown sample also increases, given that the spectrum of the unknown sample must be compared with a large number of spectra contained in the database.

Moreover, the same species of microorganisms can have a great variability in the spectral characteristics, making it difficult to compare them with the spectra contained in the database.

This variability may be due to the presence of different strains for each species, or to differences between different cultures of the same species due to possible variations in the chemical composition of the culture medium and/or growth conditions.

There is therefore the need to develop new methods to identify microorganisms that can work for a large number of species, subspecies or sub-classifications of microorganisms, and with a great variability of the reference database.

One purpose of the present invention is therefore to develop a method to identify microorganisms that is general enough to be able to identify a large number of different species, subspecies or sub-classifications of microorganisms, with high capacity for discrimination and precision.

Another purpose of the present invention is to develop a method to identify microorganisms that can identify different strains of the same species, subspecies or sub-classification of microorganisms, possibly grown in different cultures on different media, or in different environmental conditions in the presence or absence of biological fluids.

Another purpose of the present invention is to provide a method to identify microorganisms that is accurate, but that also requires rapid times for each individual analysis, even in the case of large databases.

Another purpose of the present invention is to provide an apparatus which can implement the method to identify microorganisms in a simple manner, integrating all the different steps of analysis and instrumental components.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

The present invention concerns a method to identify microorganisms, and in particular a method to allow the identification of several species, subspecies and sub-classifications of microorganisms present in an unknown sample, comparing the infrared spectrum of said unknown sample with infrared spectra of known samples, which have been previously archived in a database.

The method to identify microorganisms according to the present invention comprises:
  a step of preparing a database of reference spectra associated with known samples of species, subspecies and sub-classifications of known microorganisms;
  a step of creating pre-calculated models, or reference libraries, starting from said database, based on the most significant identification spectral characteristics, for example associated with information on shapes, sizes, intensity and peak areas of absorption, or also correlations and ratios between the intensities or between the different peak areas;
  one or more steps of sampling an unknown sample, taken from the patient, possibly subsequently grown on solid or liquid media and possibly also comprising biological fluids;
  one or more steps of acquiring the spectrum of the unknown sample;
  one or more steps of processing the spectrum of the unknown sample;
  one or more steps of analyzing the spectrum of the unknown sample, by comparing it with the pre-calculated models, each of which provides at least some belonging scores, possibly in the form of percentages, of the unknown sample to one or more of said species, subspecies or sub-classifications of known microorganisms, and a parameter of the reliability of said belonging scores;
  one or more control steps in which, starting from said belonging scores and from said reliability parameter, a new acquisition step of the spectrum of the unknown sample is requested, or a final result is provided, which can comprise a failed identification, or a successful identification.

In some embodiments, the step of preparing a database of reference spectrums associated with known sample species, subspecies or sub-classification of known microorganisms provides, for each sample, also comprises:
  a step of sampling a known sample, possibly taken from patients, possibly subsequently grown on solid or liquid media and possibly comprising biological fluids;
  one or more steps of acquiring the spectrum of the known sample;
  one or more steps of processing the spectrum of the known sample.

In some embodiments, the step of preparing the database can be carried out only once to create the database, which can then be used for each subsequent analysis of unknown samples.

In some embodiments, the step of preparing the database can also refer to the database update, to be carried out whenever it is desired to include new species, subspecies or sub-classifications of microorganisms, thus extending the range of applicability of the method.

Similarly, the pre-calculated models, once created, can be used for every subsequent analysis of unknown samples, or can also be updated every time it is desired to add new species, subspecies or sub-classifications of microorganisms.

According to the present invention, the spectra are acquired by means of an apparatus comprising an FTIR-ATR spectrophotometer.

This acquisition mode has the advantage that it obtains spectra independent of the thickness and morphology of the sample, guaranteeing a high reproducibility compared with techniques based on transmittance or reflectance.

Moreover, it allows to operate on an extremely small sample, and with extremely simple and fast operating procedures.

In some embodiments of the present invention, the FTIR-ATR spectrophotometer comprises a single-point detector, which guarantees a better signal-to-noise ratio than, for example, multipixel and/or imaging-based methods.

This characteristic also allows to limit or prevent phenomena of signal scattering and saturation and to guarantee a simpler preparation of the sample.

In some embodiments, the spectrophotometer has a continuous acquisition mode, which facilitates the cleaning of the instrument and also allows to diagnose in real time the presence of water and/or other contaminants, allowing to limit the disadvantage of the state of the art whereby the presence of water and/or contaminants can cover the peculiar signals of the microorganisms.

Advantageously, according to the present invention, spectroscopic monitoring of the drying level of the sample is provided, so that the spectrum is acquired only when a predetermined standard level of drying has been reached.

The spectra acquired with this mode therefore refer to samples that have substantially the same levels of drying, and are therefore more comparable to each other.

This characteristic allows to overcome, or at least to limit, some disadvantages of the state of the art, since no oven drying operations are necessary to remove water from the sample, thus avoiding the occurrence of irreversible effects on the microorganisms and therefore on the corresponding spectra.

In some embodiments, the present invention provides to use algorithms which automatically identify the most significant identification spectral characteristics of the samples in spectral ranges established in advance.

This characteristic allows to significantly reduce the time required by the analysis step, allowing to speed up the times and increase the accuracy of the identification.

Advantageously, the use of said pre-calculated models allows to speed up the identification times for each unknown sample, compared with methods known in the state of the art.

These characteristics allow to increase the size of the database, allowing to identify many species, subspecies or sub-classifications of different microorganisms, of different strains of the same species, subspecies or subfamily, also possibly grown in different cultures on different media, or in different environmental conditions, possibly in the presence of biological fluids.

BRIEF DESCRIPTION OF THE DRAWINGS

These and other aspects, characteristics and advantages of the present disclosure will be understood with reference to the following description, drawings and attached claims. The drawings, which are an integral part of the description, show some embodiments of the present invention and, together with the description, propose to describe the principles of the disclosure.

The present invention is described and shown better with the aid of the following drawings, in which:

FIG. 1 is a schematic representation of a possible apparatus in accordance with the method of the present invention;

FIG. 2 shows a block diagram in which the steps of one embodiment of the method of the present invention are shown by way of example;

FIG. 3a shows the raw data collected, wherein each species is represented by a different color, while FIG. 3b shows the data transformed;

FIG. 7 shows: panel a), representation of the PCA space colored as positive GRAM (light gray) and negative GRAM (dark gray); panel b), confusion matrix showing the "Predicted" data with respect to the "Actual" data obtained by the method; panel c), results of the performance of the mathematical method applied to the embodiments described here in predicting the GRAM type;

FIG. 8 is a confusion matrix obtained by the validation through cross validation of the method according to the embodiments described here with the spectra of the database.

To facilitate comprehension, the same reference numbers have been used, where possible, to identify identical common elements in the drawings. It is understood that elements and characteristics of one embodiment can conveniently be incorporated into other embodiments without further clarifications.

DETAILED DESCRIPTION OF SOME EMBODIMENTS

Figure 3A:
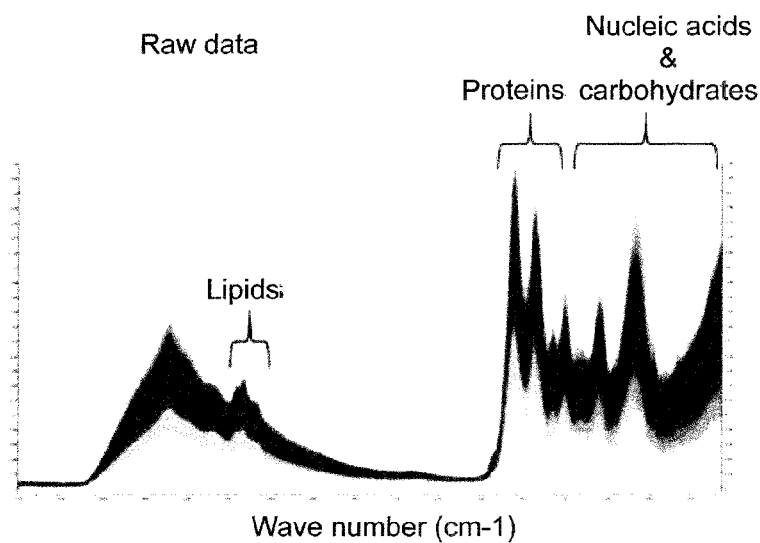
FIGS. 3a and 3b show experimental data collected using the FTIR-ATR technique, where

We will now refer in detail to the various embodiments of the present invention, of which one or more examples are shown in the attached drawings. Each example is supplied by way of illustration of the invention and shall not be understood as a limitation thereof. For example, the characteristics shown or described insomuch as they are part of one embodiment can be adopted on, or in association with, other embodiments to produce another embodiment. It is understood that the present invention shall comprise all such modifications and variants.

Before describing these embodiments, we must also clarify that the present description is not limited in its application to details of the construction and disposition of the components as described in the following description using the attached drawings. The present description can provide other embodiments and can be obtained or executed in various other ways. We must also clarify that the phraseology and terminology used here is for the purposes of description only, and cannot be considered as limitative.

Unless otherwise defined, all the technical and scientific terms used here and hereafter have the same meaning commonly understood by a person of ordinary experience in the field to which the present invention belongs.

Although methods and materials similar or equivalent to those described here may be used in practice or in the tests to verify this disclosure, the methods and materials are described below by way of example. In the event of conflict, the present application, comprising the definitions, shall prevail. The materials, methods and examples are purely illustrative and must not be understood in a restrictive manner.

Here and hereafter, by sample we mean a minimum quantity taken from a larger homogeneous set of a biological substance containing microbial organisms, such as for example microorganisms, but not only, for analysis purposes.

Sometimes, if necessary, we will specify unknown sample or known sample, in cases where the composition of microorganisms of the biological substance is, respectively, unknown or known.

In some embodiments, the species, subspecies and sub-classifications of microorganisms may be of clinical interest.

Moreover, the term "spectrum" will be used with reference to the set of electromagnetic radiations compatible with the acquisition instrument used, and therefore the terms "infrared spectrum", "vibrational spectrum" or references to vibrational transitions or certain particular spectral ranges must not be understood in a restrictive sense with respect to the applicability of the method according to the present invention.

FIG. 1 schematically shows an apparatus 10 to identify microorganisms in accordance with the present invention.

By way of example, the apparatus comprises a spectrophotometer for FTIR spectroscopy (Fourier Transform Infra-Red) in ATR (Attenuated Total Reflectance) acquisition mode, that is, a FTIR-ATR spectrophotometer, coupled with a processing system and a data display system.

The processing system and the display system can, for example, be integrated into a single processing and display system and/or can be comprised in a computer 15, such as for example a personal computer equipped with a screen.

In some embodiments, the processing system comprises a computer program, which can be memorized in a computer-readable medium and which contains instructions that can be executed on each occasion by the apparatus 10.

Hereafter, for simplicity of exposition, reference will be made to the computer 15 to indicate the set of software and hardware systems able to manage the apparatus 10, and to process and display the data.

The FTIR-ATR spectrophotometer, known per se in its main components, comprises a source 13 of infrared radiation 17, reflecting elements 16, an internal reflection element and a detector 14.

For simplicity, other components of the spectrophotometer, such as mono-chromator, chopper, interferometer, have not been shown in FIG. 1.

In some embodiments, the source 13 can be a black body source of the Globar type.

By way of example, the radiation 17 emitted by the source 13, that is, the incident radiation 17a, is directed by the reflecting elements 16 to hit the internal reflection element.

In some embodiments, the internal reflection element can be, for example, a crystal 12.

In some embodiments, the crystal 12 can be a crystal 12 with a high refraction index.

In some embodiments, the crystal 12 can be a crystal 12 of diamond, ZnSe, silicon or germanium.

Advantageously, if the crystal 12 is a diamond crystal 12, it has the advantages of being more durable than ZnSe, silicon or germanium, used in comparable measurements, and of having a greater transparency range.

The reflection of the radiation 17 inside the crystal 12 produces an evanescent field on the surface of the crystal 12, on which an acquisition zone 18 can be defined, on which the biological sample to be analyzed is positioned.

The evanescent field can penetrate for a range of depths that, depending on the case, can reach up to a few microns inside the sample.

In particular, this range of depths is a function of the angle of incidence and the wavelength of the incident radiation 17a, as well as of the refractive index of the material used for the crystal 12, and therefore can be considered substantially constant for all the samples analyzed.

For this reason, advantageously, the ATR mode allows to acquire spectra independent of the optical path of radiation through the sample, and therefore independent of the thickness of the sample, guaranteeing a higher reproducibility compared to approaches that use transmission or reflectance.

Moreover, this mode allows to limit or prevent phenomena of scattering and/or signal saturation that can negatively affect the quality of the spectrum.

This mode therefore guarantees greater repeatability of the measurement and a simpler preparation of the sample.

The radiation 17 exiting from the crystal 12 after the interaction with the sample, that is, the outgoing radiation 17b, is then directed by the reflecting elements 16 toward a detector 14.

In some embodiments, the detector 14 can be a DLaTGS detector (Deuterated L-alanine doped triglycine sulphate).

In alternative embodiments, the detector 14 can be a DTGS detector.

By way of example, the detector 14 transforms the optical information contained in the outgoing radiation 17b into electric signals, which are sent to the computer 15.

In some embodiments, the apparatus is disposed to acquire spectra in the region NIR (Near IR) and/or MIR (Mid IR) and/or FIR (Far IR).

In some embodiments, the apparatus 10 can operate in continuous acquisition mode, that is, displaying on the screen of the computer 15 in real time what is acquired on each occasion in the acquisition zone 18.

The present invention also concerns a method to identify microorganisms, shown schematically in FIG. 2 and comprising:

a step of preparing a database (A1, A2, A3) of reference spectra associated with known samples of species, subspecies and sub-classifications of known microorganisms;

a step A4 of creating pre-calculated models, starting from said database, based on identification spectral characteristics most significant for each species, subspecies or sub-classification of known microorganisms;

a step B of sampling of an unknown sample, taken from the patient, possibly grown subsequently on solid or liquid media and possibly comprising biological fluids;

one or more steps C of acquiring the spectrum of the unknown sample;

one or more steps D of processing the spectrum of the unknown sample;

one or more steps of analyzing the spectrum of the unknown sample, by comparison with the pre-calculated models, each of which analysis steps provides at least some scores, possibly in the form of percentages of the unknown sample belonging to one or more of said species, subspecies or sub-classifications of known microorganisms and a parameter of the reliability of said belonging scores;

one or more control steps F in which, starting from said belonging scores and from said reliability parameter, a new acquisition step of the spectrum C of the unknown sample is requested, or a final result of the method is provided, which can comprise a failed identification J, or a successful identification G, H, I according to different criteria.

In some embodiments of the present invention, the step of preparing a database A can in turn comprise:

a step A1 of sampling a known sample, possibly taken from patients, possibly subsequently grown on solid or liquid media and possibly comprising biological fluids;

one or more steps A2 of acquiring the spectrum of the known sample;

one or more steps A3 of processing the spectrum of the known sample.

In some embodiments, said steps A1, A2, A3 can be repeated every time a new sample known in the database is to be inserted.

In some embodiments, the sampling steps B, A1 of a sample can provide that the sample is taken from a patient.

In some embodiments, the sample taken from the patient can be subjected to preliminary analysis procedures, which provide to add nutrient substances for the microorganisms.

In some embodiments, the sample can be grown on a solid culture medium.

In some embodiments, the sample can be grown on Petri dishes.

In some embodiments, the sample can be grown on liquid culture media and then centrifuged, obtaining a concentrated pellet.

In some embodiments, the sample can be grown on liquid culture media, or liquid growth broth, and then filtered.

In some embodiments, the sample can be grown on liquid culture media, or liquid growth broth, or it can be subjected to concentration or enrichment procedures to increase the concentration of microorganisms present.

In some embodiments, the sample can possibly contain biological fluids, of human or animal origin.

In some embodiments, the spectrum acquisition steps C, A2 can provide a preliminary step of cleaning the surfaces of the apparatus in contact with the sample, for example of the acquisition zone 18 shown in FIG. 1.

In some embodiments, it is possible to acquire background spectra, for example by means of continuous acquisition mode, to verify the effectiveness of such cleaning, for example by observing the disappearance of absorption bands linked to the impurities deposited on the acquisition zone 18.

In some embodiments, the spectrum acquisition steps C, A2 also provide that an assay of the sample is taken and deposited on the crystal 12 of the spectrophotometer, for example on the acquisition zone 18, in order to acquire the spectrum.

In some embodiments, the assay is deposited on the acquisition zone 18 in a solid form, for example by removing and depositing it by means of a disposable rod.

In some embodiments, the assay can be pressed against the acquisition zone 18, for example by using a dynamometric press.

In some embodiments, the level of drying of the sample is spectroscopically monitored.

In some embodiments, it is possible to evaluate the water content leaving the apparatus in continuous acquisition mode and monitoring the reduction, up to a possible complete disappearance, of the absorption bands relating to the spectral characteristics of the water in the respective ranges of wave numbers.

According to the present invention, the spectrum is acquired when a predetermined standard level of drying of the sample is reached.

Advantageously, this characteristic allows to overcome or at least limit the problem of the state of the art whereby the spectra can have signals due to the presence of water that cover, or interfere with, the peculiar signals of the microorganisms.

This characteristic also allows to avoid procedures for drying the sample that could irreversibly modify the microorganisms to be analyzed.

The spectrum acquisition steps C, A2 also provide that the spectrum of the assay taken from the sample is recorded.

In some embodiments, the spectrum is recorded for a predetermined period of time.

In some embodiments, the spectrum is recorded for a period of time of less than 30 seconds.

In some embodiments, spectrum recording provides to acquire a predetermined number of sequential spectra, which are then averaged to improve the signal to noise ratio.

In some embodiments, a number of spectra comprised in a range of 8 to 512 for each assay can be acquired and averaged, preferably between 32 and 256 for each assay, even more preferably between 64 and 128 for each assay.

In some embodiments, the spectrum, or possibly the average of the spectra, is displayed on the screen.

The steps D, A3 of processing the spectrum, or of the average of the spectra, can provide:
- to use linear and/or non-linear interpolation and/or fitting algorithms (spectral profile);
- to calculate the first and/or second derivative of the spectral profile;
- to normalize the derivatives using a vector normalization algorithm over the entire spectral range;
- to select the most useful spectral zones for the classification of the species, subspecies or sub-classifications of microorganisms.

By way of example, the spectral zones can comprise: the range 950-1280 $cm^{-1}$ for nucleic acids, carbohydrates and polysaccharides; 1280-1480 $cm^{-1}$ for starches, for example proteins, methyl and methylenes, for example lipids; 1700-1800 $cm^{-1}$ for the carbonyl groups, for example of lipids; 2800-3000 $cm^{-1}$ for aliphatic chains, for example lipids.

In some embodiments, artificial learning algorithms (machine learning) can be used to improve the selection process of the spectral ranges.

Figure 3B:
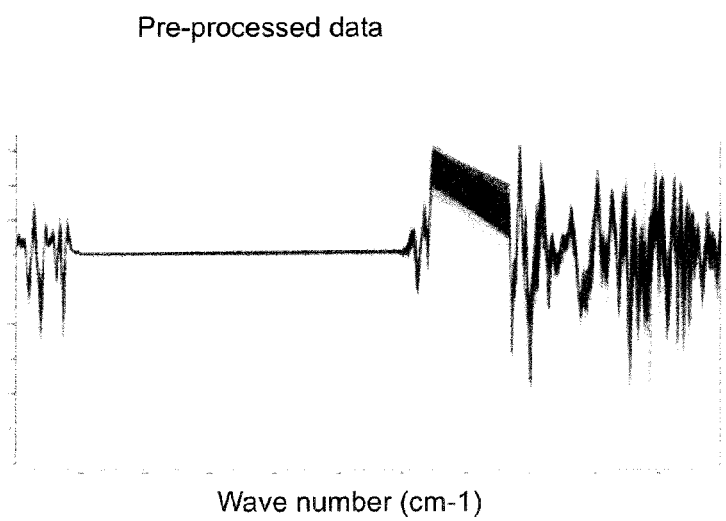

By way of example, FIG. 3a shows the spectra that can be collected for different samples, while FIG. 3b shows the processed spectra.

FIG. 3a also shows by way of example some identification spectral characteristics significant for the purposes of the method of the present invention.

In some embodiments, the spectral regions and identification spectral characteristics are then used to classify and subsequently identify the individual species, subspecies or sub-classifications of microorganisms.

In some embodiments, an automatic recognition system is provided, to identify the spectral ranges and the identification spectral characteristics of greatest interest.

Advantageously, the presence of different chemical classes, such as for example nucleic acids, lipids, proteins, carbohydrates, and other constituents of microorganisms, allows to obtain characteristic signals for each species, subspecies or sub-classification of microorganisms, so that it is possible to obtain a predictive method.

By repeating steps A1, A2, A3 for several known samples, it is possible to prepare the database of reference spectra of species, subspecies or sub-classifications of known microorganisms.

However, in some embodiments of the present method it is also provided that the database can comprise spectra of species, subspecies or sub-classifications of known microorganisms obtained using other methods.

In some embodiments, the database comprises spectra relating to monomicrobial cultures belonging to different species, subspecies or sub-classifications of known microorganisms.

In some embodiments, the database comprises spectra relating to different strains of known microorganisms for each species, subspecies or sub-classification of known microorganisms.

In some embodiments, the database comprises spectra relating to samples grown on different culture media, for example but not only Agar, CNA Agar, CLED Agar, Blood Agar, Chromogenic Agar.

In some embodiments, the database comprises spectra relating to samples grown in a liquid-phase growth broth, which are then centrifuged, or filtered, or enriched, to obtain pellets or concentrated samples.

Advantageously, the spectra obtained by growth in liquid broth and subsequent pelletizing or filtration, can be used as standard reference spectra, since they do not contain interferences deriving from matrices of solid-phase growth media.

Advantageously, measurements of spectra obtained from growth in liquid broth and subsequent pelletizing or filtration or enrichment allow to identify the spectra directly in the presence of biological fluids, for example bodily fluids.

This heterogeneity and variability of the spectra contained in the database allows to perform a general analysis, which allows to identify many species, subspecies or sub-classifications of microorganisms, many different strains for each individual species, subspecies or sub-classification, also including effects deriving from growths on different culture media.

In the embodiments where multiple acquisitions of each spectrum are used, it is possible to insert in the database the individual spectra repeated and/or the average spectrum calculated on the repetitions.

The pre-calculated models, or reference libraries, created or updated in step A4, can be based on the most significant identification spectral characteristics for the purposes of the analysis in the spectral ranges selected.

In some embodiments, the most significant identification spectral characteristics can be associated, for example, with information on shapes, sizes, intensities and areas of absorption peaks, or also correlations and ratios between the intensities or between the areas of different peaks.

In some embodiments, the pre-calculated models can comprise a list of identification spectral characteristics significant for each known sample of species, subspecies or sub-classification of known microorganisms.

In some embodiments, the most significant identification spectral characteristics can be identified by said statistical analysis techniques, and/or approaches based on neural networks and/or artificial learning.

These pre-calculated models allow to quickly and automatically identify the most significant identification spectral characteristics for the purposes of comparison.

In this way, every time two spectra are compared, the comparison can be performed only in the spectral ranges and/or in relation to the spectral characteristics of greatest interest, rather than on the whole spectral range and/or for all the spectral characteristics.

For example, if one wanted to compare, over the entire spectral range, a spectrum of an unknown sample acquired with a resolution of 1 cm$^{-1}$, with a database that contains, by way of example, 18000 reference spectra acquired with the same resolution, this comparison, using the methods of the state of the art, would require the evaluation of 65 million points.

Applicant has found that, by using the methods according to the present invention, working on selected spectral ranges and with the pre-calculated models, this comparison can require a number of evaluations of points between 20 and 80 times lower than the methods of the state of the art.

Using pre-calculated models therefore allows to significantly reduce the analysis times for each unknown sample, even in the presence of large databases.

This characteristic therefore allows to considerably increase the size of the databases to comprise a high number of species, subspecies or sub-classifications of known microorganisms, thus improving and extending the predictive and identification capabilities of the method of the present invention.

This characteristic also allows to work with spectra even at high resolution, improving the accuracy and precision of the method.

Moreover, for example, the presence of the list can make it superfluous to use least-squares methods and/or possible calculations of average square discards on the whole range of wave numbers for all the spectra.

In other embodiments, it is provided to use artificial learning (machine learning) and artificial intelligence models, to improve the automatic recognition system and the pre-calculated models, progressively as the method is used.

In some embodiments, the analysis step E provides that the spectrum of the unknown sample is compared with reference spectra contained in the reference database and/or with pre-calculated models.

In some embodiments of the present invention, statistical techniques can be used for this comparison.

In some embodiments of the present invention, the statistical techniques can comprise multivariate analysis, for example Principal Components Analysis (PCA), or Linear Discriminant Analysis (LDA), also Linear Discriminant partial least-squares (LDPLS), Quadratic Discriminant Analysis (QD).

In some embodiments, methods, techniques or algorithms that implement approaches based on neural networks can be used for said comparison.

In some embodiments, methods, techniques or algorithms that implement approaches based on artificial learning (machine learning) can be used for said comparison.

In some embodiments of the present invention, said comparison can also provide to compare the derivatives, first and/or second, of the spectra.

In some embodiments, it is possible to use statistical weights to weigh different regions of the spectra in different ways.

In some embodiments of the present invention, the comparison between two spectra can be performed by means of a definition of distance between two spectra, for example using methods based on least-squares.

In some embodiments, the distance can be used as a metric to perform statistical and/or chemometric analyses.

In some embodiments, the variance between spectra can be used for the PCA analysis.

In some embodiments, the analysis step E provides a score, for example a percentage, of the unknown sample belonging to one or more of the species, subspecies or sub-classifications, represented in the database.

In some embodiments, the analysis step E provides a reliability parameter that estimates the reliability of the analysis, and in particular the belonging score.

In some embodiments, the control step F provides to process the belonging score and the reliability parameter.

According to some embodiments, a belonging score is considered immediately reliable if the reliability parameter of the analysis is higher than a pre-set level of acceptability. For example, if percentage scores are used, the level of acceptability can be chosen in a range comprised between 80% and 100% (block G in FIG. 2).

In some embodiments, if it is not possible to identify the unknown species, subspecies or sub-classification of microorganisms in an unequivocal manner at the first attempt, it is possible to repeat steps C, D, E and F to add new data and improve the result of the analysis.

In some embodiments, this can be provided if the reliability parameter is lower than a second preset level of acceptability. For example, in the embodiments that use scores expressed as a percentage, this second level can be selected in a range comprised between 70% and 80%.

In this case, the method provides a second acquisition step C, a second processing step D and a second analysis step E to be carried out on a second assay taken from the unknown sample.

For example, the second assay can be a different colony of microorganisms, taken from the same Petri dish on which the unknown sample was cultivated and grown.

If the sample is in pellet form, the second assay can be taken, for example, with a disposable rod from the same concentrated pellet from which the first one was taken.

Afterward, if the reliability of the result of the second analysis is again lower than a third preset level of acceptability, for example numerically equal to the second level of acceptability, the method provides to compare the similarity between the two spectra obtained with the first acquisition step C and with the second acquisition step C.

If the spectra are found similar (block H in FIG. 2), the method supplies, as the result of the analysis, the belonging scores of the unknown sample to one or more species, subspecies or sub-classifications of microorganisms, in agreement between the two acquisitions.

If the spectra are found to be discordant, it is provided that a third assay is taken, and a third acquisition step C, a third processing step D and a third analysis step E are performed.

If at least two of the three spectra are found similar (block I in FIG. 2), the method provides, as the result of the analysis, the belonging scores of the sample to the species, subspecies or sub-classifications of the microorganisms of the database, in agreement with two of the three spectra.

Otherwise (block J in FIG. 2), a message of non-identification is displayed, together with the spectra and the three belonging scores relating to the three acquisitions.

One embodiment provides a computer program, or software, used to collect the data and analyze them with respect to the database, which can be memorized in a computer-readable medium and which contains instructions which, once executed by an analysis apparatus for the classification and identification of microorganisms, determine the execution of the method according to the present description.

Example 1

Figure 4:
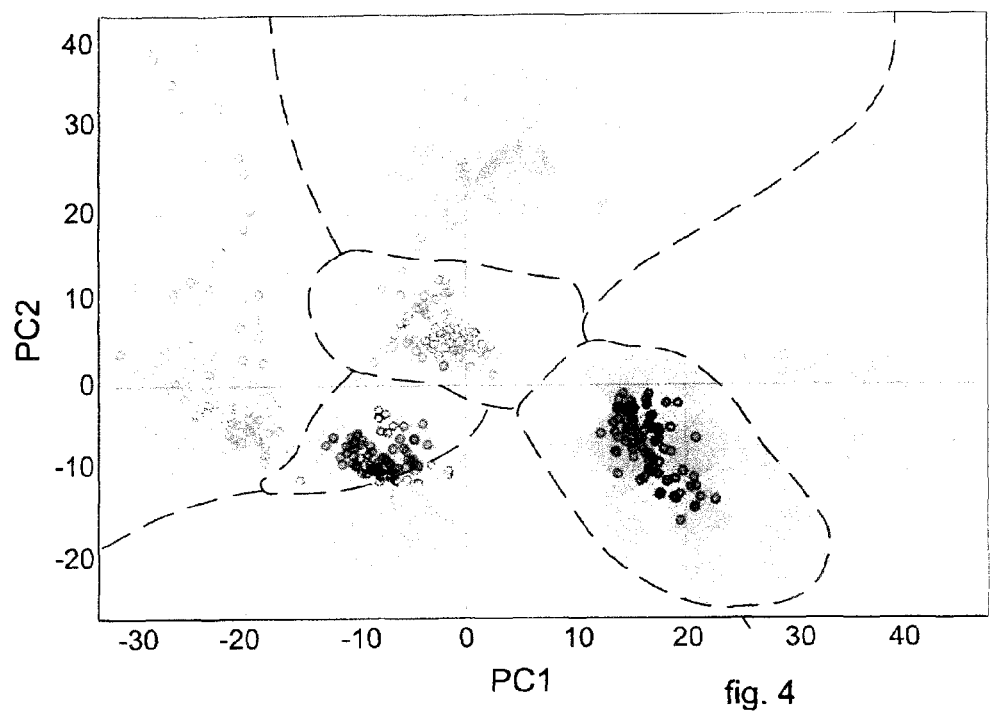
FIG. 4 schematically shows the zones of the clusters obtained using PCA in the space of two principal components, corresponding to the spectra of different species of microorganisms.

By way of example, FIG. 4 shows schematically the results of a PCA analysis of the spectra contained in a database in accordance with the present invention.

In particular, each point in FIG. 4 corresponds to the spectrum, or to the average of the spectra acquired, relating to a species, subspecies or sub-classifications of microorganisms, oriented along the first two principal components.

The spectra have also been grouped into zones, the extension of which is connected to the variability of the spectra of each species, subspecies or sub-classifications of microorganisms, based on the different strains and/or different culture media for each sample.

Example 2

Figure 5:
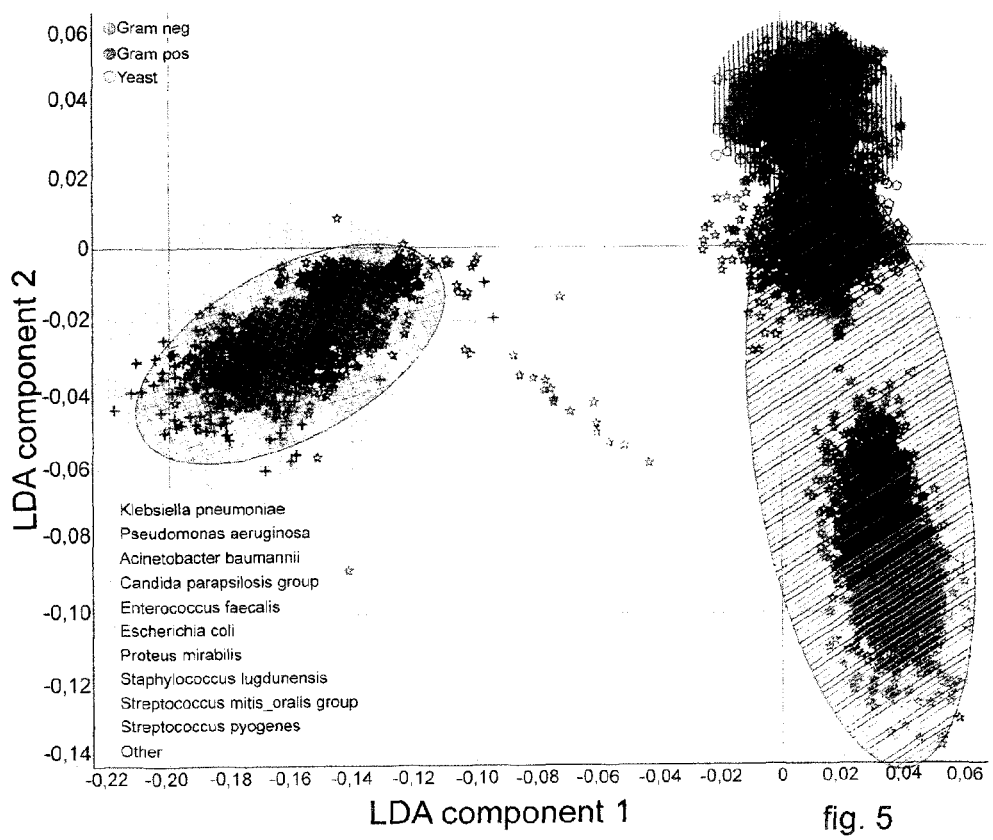
FIG. 5 schematically shows an example of zones of the clusters obtained using LDA in the space of the first two components.

By way of example, FIG. 5 schematically shows the results of an LDA analysis of the spectra contained in a database according to the present invention.

In particular, each point in FIG. 5 corresponds to the spectrum, or to the average of the spectra acquired, relating to a species, subspecies or sub-classifications of microorganisms, oriented along the first two components.

The spectra have also been grouped into zones, the extension of which is related to the variability of the spectra of each species, subspecies or sub-classifications of microorganisms, based on the different strains and/or different culture media for each sample.

Example 3

In one embodiment, a database according to the present invention has been obtained by sowing selected and certified NNCCLS type Atlanta microorganisms in Petri dishes or on liquid medium.

In this embodiment, specific spectra were obtained for each individual microorganism sown on a Petri dish or on liquid medium; moreover, each single strain was sown in various growth media, using Petri dishes from various producers of liquid media, in order to verify the variability of the spectra with respect to the growth conditions.

The media used was selected from:
CLED Agar
MacConkey Agar
CNA Agar
Blood agar

For each microorganism, 500 growths of microorganisms were obtained in order to have a broad and complete case study with regard to obtaining a numerical cluster able to verify the correlation of the data compared with other methods in use.

Figure 6:
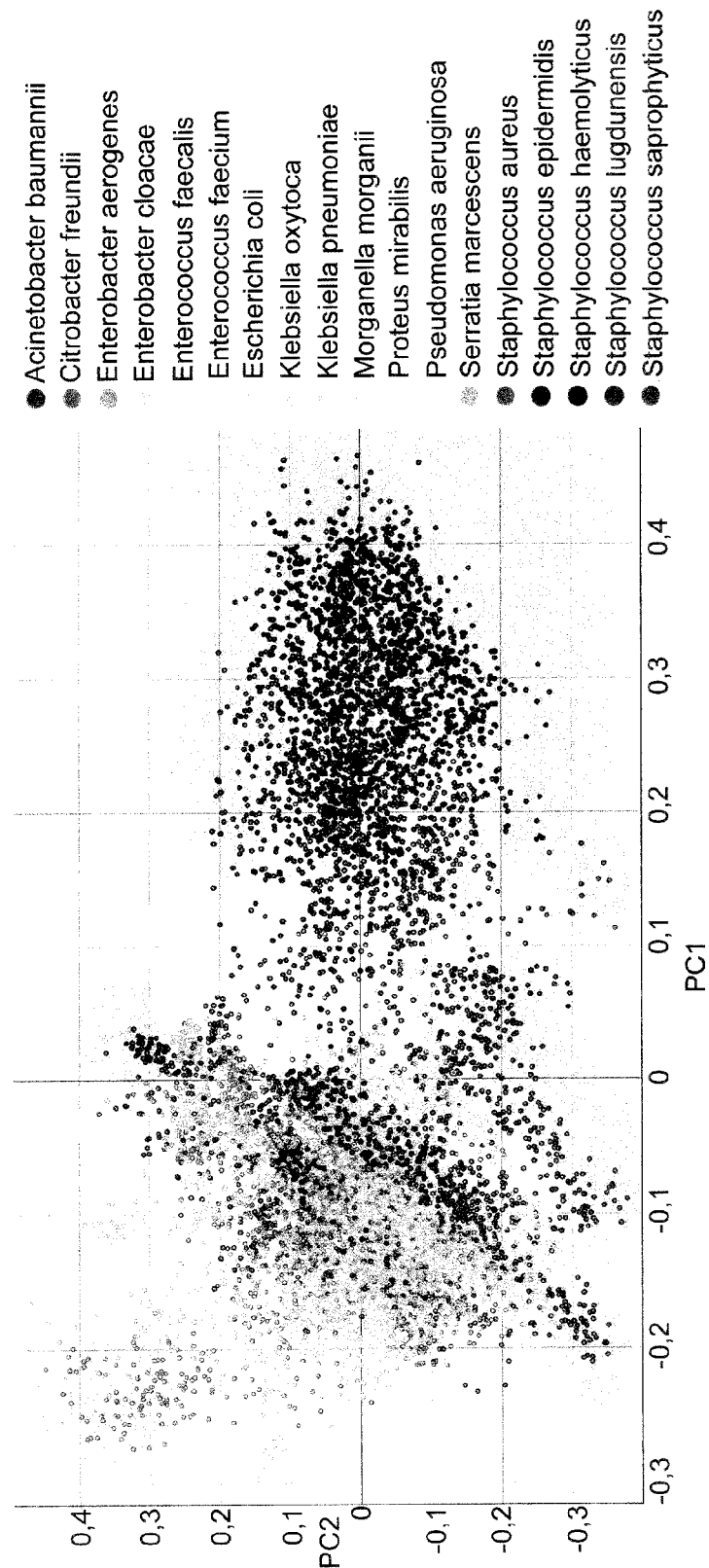
FIG. 6 schematically shows an example of zones of the clusters obtained using PCA in the space of two principal components, corresponding to the spectra of different species of microorganisms.

FIG. 6 represents the data acquired in the space of the first two principal components in which each species is represented by a different shade of gray.

Example 4

In one embodiment, the method according to the invention can be used to predict the GRAM-type microorganism. An example of the results on the GRAM+GRAM classification—is shown in FIG. 7.

Panel a) in FIG. 7 is a representation of the PCA space colored as positive GRAM (light gray) and negative GRAM (dark gray).

Panel b) in FIG. 7 is the confusion matrix showing the "predicted" data compared with the "actual" data obtained from the method.

Panel c) in FIG. 7 shows the performance results of the mathematical method in predicting the GRAM type.

Example 5

In one embodiment, the method can be used to identify species, subspecies or sub-classifications of microorganisms. See FIG. 8, which shows a confusion matrix obtained from the validation of the method with the spectra of a database according to the present invention, in which a correspondence from 99.9% to 96% can be observed between the actual and the predicted.

It is clear that modifications and/or additions of parts or steps can be made to the method and/or apparatus as described heretofore, without departing from the field and scope of the present invention. It is also clear that, although the present invention has been described with reference to some specific examples, a person of skill in the art shall certainly be able to achieve many other equivalent forms of method and/or apparatus, having the characteristics as set forth in the claims and hence all coming within the field of protection defined thereby.

The invention claimed is:

1. A method to identify microorganisms in a biological sample, using an infrared spectroscope with attenuated total reflectance comprising:
   a step of preparing a database of reference spectra associated with known samples of species, subspecies and sub-classifications of known microorganisms;
   one or more steps of creating pre-calculated models, starting from said database, based on identification spectral characteristics most significant for each species, subspecies or sub-classification of known microorganisms;
   a step of sampling an unknown sample, obtained from growth on solid or liquid media, possibly with biological fluids;
   one or more steps of acquiring the spectrum of the unknown sample;
   one or more steps of processing the spectrum of the unknown sample;

one or more steps of analyzing the spectrum of the unknown sample, by comparing it with the pre-calculated models, each of which provides at least some belonging scores of the unknown sample to one or more of said species, subspecies or sub-classifications of known microorganisms and a parameter of the reliability of said belonging scores;

one or more control steps in which, starting from said belonging scores and from said reliability parameter, a new acquisition step of the spectrum of the unknown sample is requested, or a final result of the method is provided, which can comprise a failed identification, or a successful identification;

wherein the acquisition steps provide spectroscopic monitoring of the drying level of the sample, so that the spectrum is acquired only when a predetermined standard level of drying is reached.

2. The method as in claim 1, wherein the steps of preparing a database of reference spectrums associated with known sample species, subspecies or sub-classification of known microorganisms provides, for each known sample:

a step of sampling the known sample obtained by growth on solid or liquid media in the presence or absence of biological fluids;

one or more steps of acquiring the spectrum of the known sample;

one or more steps of processing the spectrum of the known sample.

3. The method as in claim 1, wherein the reference spectra comprise spectra associated with samples of different species, subspecies or sub-classifications of microorganisms and/or of different strains of the same species, subspecies or sub-classifications of microorganisms and/or grown on variable culture media, with or without biological fluids.

4. The method as in claim 1, wherein the unknown sample is grown on a solid culture medium.

5. The method as in claim 1, wherein at least one of the known samples is grown on a solid culture medium.

6. The method as in claim 1, wherein the unknown sample is grown in at least one growth liquid broth, subsequently centrifuged or filtered or enriched to obtain a pellet or a concentrated sample, and in that the spectrum is acquired by removing assays from said pellet or concentrated sample.

7. The method as in claim 1, wherein at least one of the known samples is grown in at least one growth liquid broth, subsequently centrifuged or filtered or enriched to obtain a pellet or a concentrated sample, and in that the spectrum is acquired by removing assays from said pellet or concentrated sample.

8. The method as in claim 1, wherein the processing step provides to use algorithms which automatically identify the most significant identification spectral characteristics of the samples in spectral ranges defined in advance.

9. The method as in claim 1, wherein the analysis step provides to use statistical methods such as multivariate analysis.

10. The method as in claim 1, wherein the analysis step provides to use methods based on the analysis of the principal components.

11. The method as in claim 1, wherein the analysis step provides to use methods based on neural networks.

12. The method as in claim 1, wherein the analysis step provides to use methods based on the analysis of clusters of spectra.

13. The method as in claim 1, wherein said pre-calculated models comprise a list of said identification spectral characteristics for each sample, both unknown and known.

14. An apparatus to carry out the method to identify microorganisms in a biological sample as in claim 1, comprising a spectrophotometer for FTIR spectroscopy in ATR acquisition mode, coupled with a processing system and a data display system installed in a computer, a source of infrared radiation, reflecting elements, an internal reflection element, such as a crystal, and a detector, an acquisition zone being defined on the surface of said crystal on which the biological sample to be analyzed is positioned, wherein in said computer said pre-calculated models associated with known samples of species, subspecies and sub-classifications of known microorganisms are memorized.

* * * * *